US006660041B1

(12) United States Patent
Grundei

(10) Patent No.: US 6,660,041 B1
(45) Date of Patent: Dec. 9, 2003

(54) HOLLOW RASP FOR PREPARING A TUBULAR BONE

(75) Inventor: Hans Grundei, Lübeck (DE)

(73) Assignee: Eska Implants GmbH & Co. (DE)

( * ) Notice: Subject to any disclaimer, the term of this patent is extended or adjusted under 35 U.S.C. 154(b) by 0 days.

(21) Appl. No.: 09/890,430

(22) PCT Filed: Jan. 7, 2000

(86) PCT No.: PCT/EP00/00066
§ 371 (c)(1),
(2), (4) Date: Jul. 31, 2001

(87) PCT Pub. No.: WO00/45715
PCT Pub. Date: Aug. 10, 2000

(30) Foreign Application Priority Data

Feb. 1, 1999 (DE) .......................... 199 03 683

(51) Int. Cl.$^7$ ................................. A61F 2/36
(52) U.S. Cl. ............... 623/23.26; 623/23.5; 623/23.53; 606/85
(58) Field of Search .............. 623/23.53, 23.26, 623/22.12, 23.44, 23.5; 606/85

(56) References Cited

U.S. PATENT DOCUMENTS 5,707,374 A * 1/1998 Schmidt ...................... 606/85
5,814,049 A * 9/1998 Pratt et al. .................... 606/80
5,885,295 A * 3/1999 McDaniel et al. ............ 606/86

FOREIGN PATENT DOCUMENTS

| DE | 195 43 530 | 5/1990 |
| DE | 39 07 256 | 9/1990 |
| EP | 0 634 145 | 1/1995 |
| WO | WO 98 26725 | 6/1998 |

* cited by examiner

Primary Examiner—Corrine McDermott
Assistant Examiner—Crystal Gilpin
(74) Attorney, Agent, or Firm—Cantor Colburn LLP

(57) ABSTRACT

The invention relates to a hollow rasp for preparing a tubular bone in which a post-shaped endoprosthesis is inserted. A manipulating instrument can be proximally coupled to the rasp. The rasp comprises a metal grid network and a plurality of metal rasp elements. The metal rasp elements are studded at least at junctions of the metal grid network and are an integral part of a material forming the grid network.

8 Claims, 1 Drawing Sheet

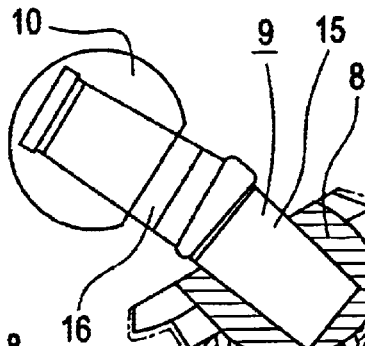
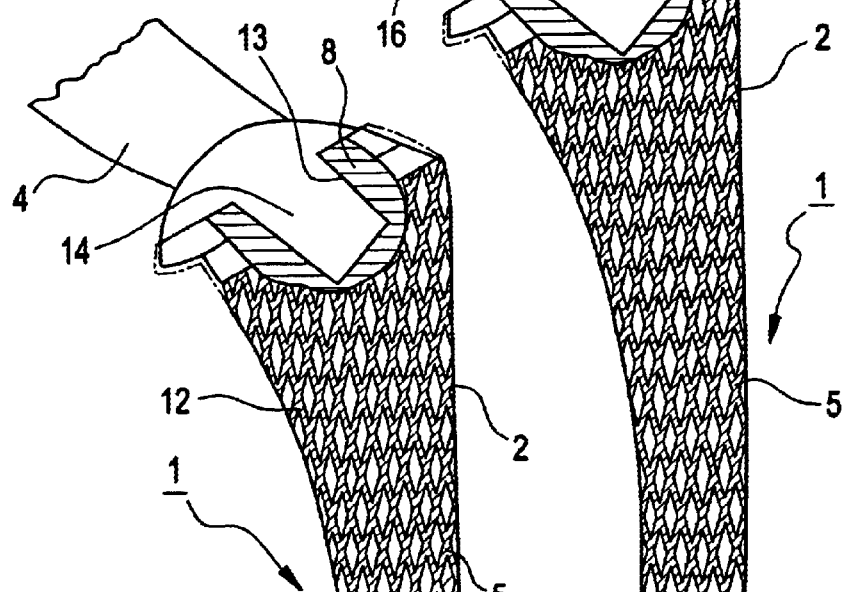
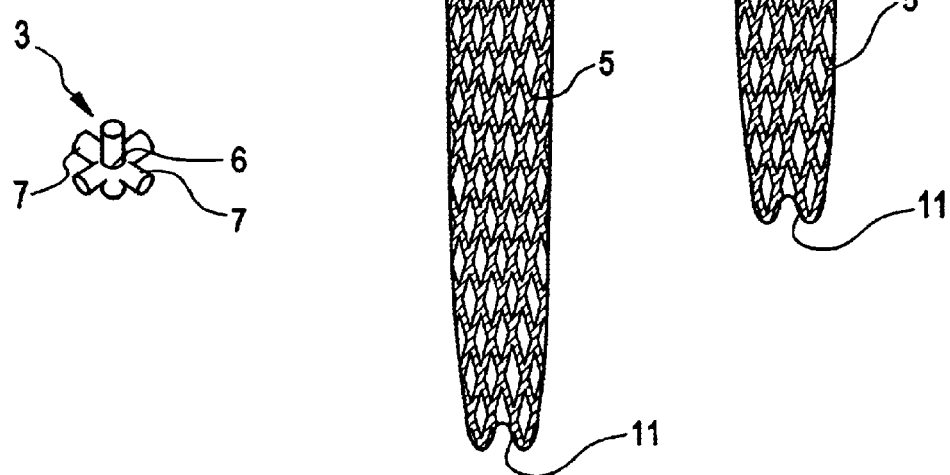

HOLLOW RASP FOR PREPARING A TUBULAR BONE

FIELD OF THE INVENTION

The invention concerns a hollow rasp for preparing a tubular bone for the insertion of a post-shaped endoprosthesis.

DESCRIPTION OF THE RELATED ART

Before the implantation of a post-shaped endoprosthesis in a tubular bone, for example in the human femur, the bone is resected on the joint end, the spongiosa is routed and the bone marrow is removed. The post part of the endoprosthesis can then be placed in the routed space, where it is fixed with or without using cement. A typical example of this type of post-shaped endoprosthesis is a hip post in an artificial hip joint. Hollow rasps are known from the state of the art, for example, DE-U-9212906 and DE-A-4323873.

The hollow rasp in the last publication mentioned is different from the hollow rasp in the first publication mentioned basically in that its hollow tube has a medial longitudinal slit. This gives it better routing action than the rasp in the first publication mentioned. When used, it also substantially reduces the risk of thromboses and/or emboli, which go back to increased excretion of bone marrow fat, which can cause fat emboli in the patient.

The hollow-shaft rasp in the last publication mentioned is basically composed of spring steel with a scraper profile, which is designed so that it only works in one direction of movement of the rasp. During routing, excavated material is pushed inside the hollow tube.

In practice, it has been shown that the scraper profile used in the state of the art is not sharp enough to clear out the tubular bone quickly.

On this background, the problem of this invention is to propose a hollow rasp of the type mentioned at the beginning which has much greater rasping action than the hollow rasp in the state of the art.

SUMMARY OF THE INVENTION

The invention provides that the hollow rasp, to which a manipulating instrument can be coupled, be composed of a metal grid network, which is studded with metal rasp elements, at least at its junctions, which are an integral part of the material forming the grid network.

In particular, the hollow rasp in the invention is produced using a fine-casting wax melting method so that the rasp elements also remain bonded to the grid network even under high stress. The rasp elements work in all directions of movement.

Due to the rotationally symmetric design of the hollow rasp, it is also possible to set the hollow rasp with the manipulating instrument into a corresponding motor-driven machine and to use the hollow rasp as a motor-driven cutter. The rasp elements designed to be integral with the grid network definitely withstand these high stresses.

The bone marrow scraped off during the routing process and the scrapped off spongiosa are forced inside the grid network to prevent any risk of emboli or thromboses.

For continuous rasping or cutting, it is an advantage if a suction unit can be connected to the proximal side of the hollow rasp, and the cut or scraped off components can be suctioned off, as is known per se.

In one especially preferred form of embodiment, the rasp elements are composed of a basic body with at least three pegs projecting from it. This design gives a bone rasp aggressiveness unknown in the past.

In an advantageous variation, the hollow rasp in the invention basically has the outer contours of the endoprosthesis to be implanted. This is no problem because of a technically fine casting production process, unlike many state-of-the-art hollow rasps.

One special aspect is that the hollow rasp itself can remain as an implant in the routed bone marrow space. In other words, the hollow rasp can be used as such and then remain in the hollow space made by it. The aggressiveness of the surface and its hollow space allow bone material to organize relatively fast in the hollow space and grow around the rasp elements. One special advantage then is the possibility of uncoupling the manipulating instrument from the hollow rasp and, for example providing it with a joint ball by means of a double cone, whereupon the post part of an artificial hip joint is made from the hollow rasp.

BRIEF DESCRIPTION OF THE DRAWINGS

The invention will be explained in greater detail using an example of embodiment.

FIG. 1 is a schematic view of a hollow rasp with a manipulating instrument coupled to it and an enlarged view of a rasp element, and FIG. 2 shows a way of turning the hollow rasp into an implant after it performs its rasping function.

DETAILED DESCRIPTION OF THE PREFERRED EMBODIMENT

The same reference numbers are used for the same parts below.

FIG. 1 shows an example of a hollow rasp 1 in roughly the shape of a post part of an artificial hip joint. The hollow rasp 1 basically consists of a metal grid network 2, with corresponding apertures, through which the excavated material is pushed inside the hollow rasp 1. For this reason, an aperture 11 is also provided on the distal end, through which spongiosa and/or bone marrow is pushed inside the hollow rasp 1 when the hollow rasp 1 is driven into the tubular bone. At the junctions 5 of the grid network 2, and at the webs 12 in between are rasp elements 3, which here have six pegs 7 projecting from a basic body 6. The pegs 7 give the hollow rasp 1 tremendous aggressiveness.

An adapter piece 8 is provided on the proximal side with a casing 13, shown by way of example here, for a cone 14 of a manipulating instrument 4, which can be attached to the proximal part of the hollow rasp 1.

FIG. 2 shows the same hollow rasp 1, but as it is already reworked, after a free space has been made with it in the tubular bone concerned for the implant, which is formed by the rasp 1 itself here.

The insertion cone 14 of the manipulating instrument 4 in FIG. 1 has been replaced here by a double cone 9 with two insertion cones 15 and 16. Then an artificial ball 10 of an artificial joint was set on the insertion cone 16. The hollow rasp 1 thus forms a complete implant in the form of the post part of an artificial hip joint.

What is claimed is:

1. A hollow rasp for preparing a tubular bone for insertion of a post-shaped endoprosthesis, to which a manipulating instrument can be coupled proximally, the hollow rasp comprising a metal grid network and a plurality of metal rasp elements, wherein the metal rasp elements are studded at least at junctions of the metal grid network and wherein the metal rasp elements are an integral part of a material forming the grid network.

2. The hollow rasp in claim 1, wherein each of the rasp elements comprises a basic body and at least three pegs projecting from the basic body.

3. The hollow rasp in claim 1, to which a suction unit can be connected proximally.

4. The hollow rasp in claim 1, wherein the hollow rasp basically has outer contours of the endoprosthesis to be implanted.

5. A method of using the hollow rasp in claim 1 as an implant left in a tubular bone after a marrow space is routed.

6. The hollow rasp in claim 2, to which a suction unit can be connected proximally.

7. The hollow rasp in claim 2, wherein the hollow rasp basically has outer contours of the endoprosthesis to be implanted.

8. The hollow rasp in claim 3, wherein the hollow rasp basically has outer contours of the endoprosthesis to be implanted.

* * * * *